(12) United States Patent
Kimmell et al.

(10) Patent No.: US 8,882,717 B2
(45) Date of Patent: Nov. 11, 2014

(54) MULTI-SITE INJECTION SYSTEM

(75) Inventors: Steven D. Kimmell, Granada Hills, CA (US); Scott J. Gerondale, Newbury Park, CA (US)

(73) Assignee: Allergan, Inc., Irvine, CA (US)

( * ) Notice: Subject to any disclaimer, the term of this patent is extended or adjusted under 35 U.S.C. 154(b) by 1914 days.

(21) Appl. No.: 10/599,829

(22) PCT Filed: Apr. 11, 2005

(86) PCT No.: PCT/US2005/012122
§ 371 (c)(1),
(2), (4) Date: Jul. 29, 2009

(87) PCT Pub. No.: WO2005/110525
PCT Pub. Date: Nov. 24, 2005

(65) Prior Publication Data
US 2010/0256594 A1    Oct. 7, 2010

Related U.S. Application Data

(60) Provisional application No. 60/561,378, filed on Apr. 12, 2004, provisional application No. 60/561,400, filed on Apr. 12, 2004, provisional application No. 60/561,389, filed on Apr. 12, 2004, provisional application No. 60/561,395, filed on Apr. 12, 2004, provisional application No. 60/561,480, filed on Apr. 12, 2004, provisional application No. 60/561,390, filed on Apr. 12, 2004.

(51) Int. Cl.
*A61M 5/00* (2006.01)
*A61M 37/00* (2006.01)

(52) U.S. Cl.
CPC ... *A61M 37/0015* (2013.01); *A61M 2037/0023* (2013.01)
USPC ............................................ 604/173; 604/46

(58) Field of Classification Search
CPC ................... A61B 17/205; A61B 2017/00747; A61K 9/0021; A61M 35/003; A61M 37/0015; A61M 2037/0023; A61M 2037/003; A61M 2037/0038
USPC .......... 604/21, 22, 46, 47, 173, 506; 606/167, 606/183, 186
See application file for complete search history.

(56) References Cited

U.S. PATENT DOCUMENTS 1,688,332 A * 10/1928 Heck, Jr. et al. ............... 604/156
4,823,806 A *  4/1989 Bajada .......................... 600/557
(Continued)

FOREIGN PATENT DOCUMENTS

DE    2319591 A1    11/1974
DE    19518974      11/1995
(Continued)

OTHER PUBLICATIONS

"foam rubber." Encyclopaedia Britannica. Encyclopaedia Britannica Online Academic Edition. <http://www.britannica.com/EBchecked/topic/211789/foam-rubber>.*
"foam rubber." American Heritage Dictionary. <http://www.answers.com/topic/foam-rubber>.*

*Primary Examiner* — Kami A Bosworth
(74) *Attorney, Agent, or Firm* — Linda Allyson Fox

(57) ABSTRACT

A multi-site injection system (10) in accordance with the present invention generally includes a plurality of medicament delivering needles/microprotrusions (18) along with a support therefore. A supply of medicament (36) is provided and a means provided for supplying the medicament to the plurality of needles/microprotrusions in order to effect delivery into a stratum corneum (42) of a user.

4 Claims, 12 Drawing Sheets

(56) References Cited

U.S. PATENT DOCUMENTS 5,139,029 A * 8/1992 Fishman et al. .............. 600/556
6,475,160 B1 * 11/2002 Sher .............................. 600/556
2004/0087992 A1 * 5/2004 Gartstein et al. ............. 606/186

FOREIGN PATENT DOCUMENTS

FR           2720003 B1    6/1998
WO      WO 03/024518 A2    3/2003

* cited by examiner

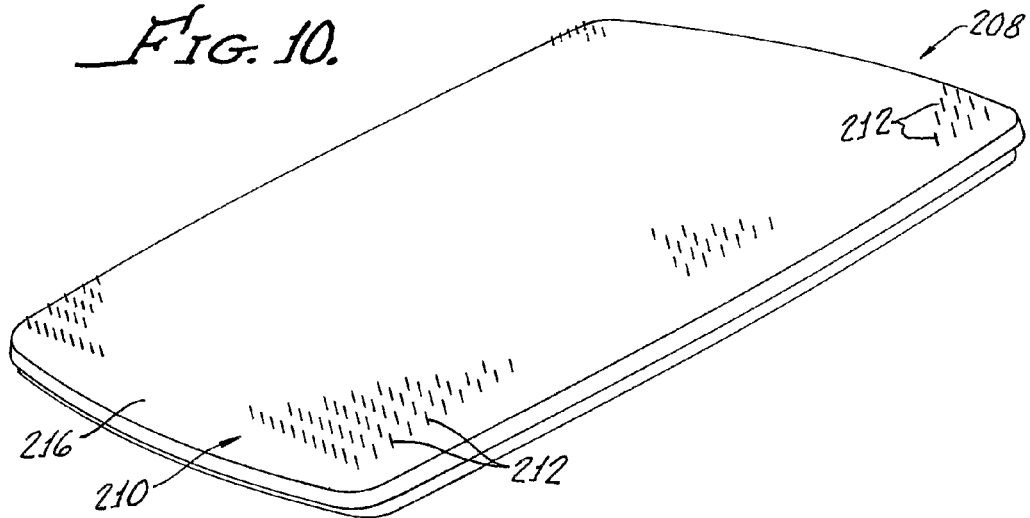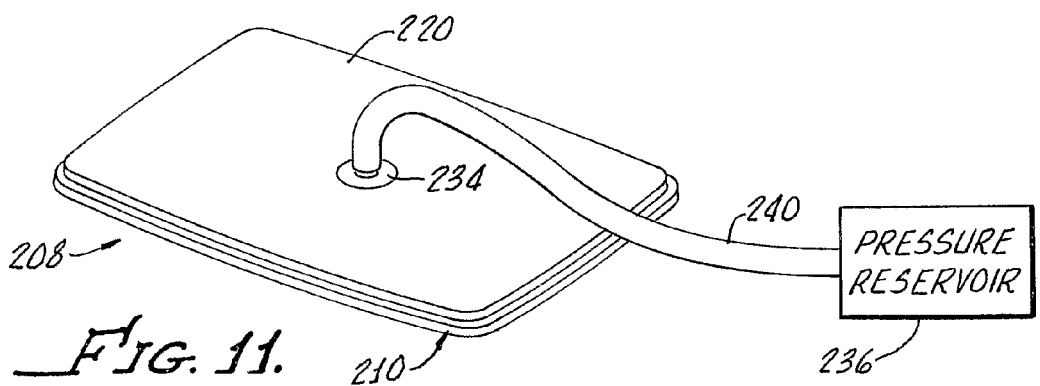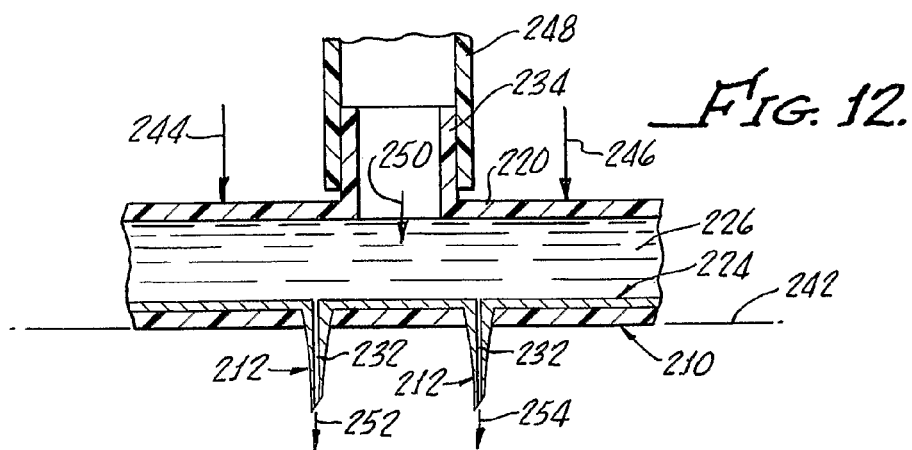

MULTI-SITE INJECTION SYSTEM

This application is a national stage application under 35 USC 371 of PCT Patent Application No. PCT/US2005/012122, filed Apr. 11, 2005, which claims priority to U.S. Provisional Patent Application No. 60/561,378, filed Apr. 12, 2004; U.S. Provisional Patent Application No. 60/561,400, filed Apr. 12, 2004; U.S. Provisional Patent Application No. 60/561,389, filed Apr. 12, 2004; U.S. Provisional Patent Application No. 60/561,395, filed Apr. 12, 2004; U.S. Provisional Patent Application No. 60/561,480, filed Apr. 12, 2004; and U.S. Provisional Patent Application No. 60/561,390, filed Apr. 12, 2004.

The present invention is generally directed to the administration of a medicament and is more particularly directed to a multi-site injection system for dermal delivery of a medicament.

Topical delivery of medicament is a very useful method for achieving both systemic and localized pharmalogical effects. A problem in such transcutaneous drug delivery is providing sufficient drug penetration across the skin.

As is well know, the skin consists of multiple layers, starting with a stratum corneum layer of about 20 microns for humans, a viable epidermal tissue layer of about 70 microns and a dermal layer of about 2 mm in thickness.

As such, the stratum corneum represents a major barrier for chemical penetration through the skin being responsible for the majority of the skin barrier property. This is, of course, dependent upon the medicament water solubility and molecular weight.

Delivering medicament through the skin may be attained by piercing the stratum corneum and delivering a drug to the skin in or below the stratum corneum. Such devices for piercing the stratum corneum may include a plurality of micron-sized needles or blades having lengths sufficient to pierce the stratum corneum without passing completely through the epidermis. Once a medicament is passed through the stratum corneum, there typically is no major hindrance to penetration of the remaining epidermal layers or the dermis.

Do to sometimes painful use of individual needle penetration of the stratum corneum, it is desirable to provide a plurality of micro needles or protrusions for simultaneous delivery of a medicament through a larger area of stratum corneum.

Accordingly, the present invention provides for a multi-site injection system utilizing a plurality of microprotrusions or needles for piercing the stratum corneum of the skin to a depth sufficient for delivering a medicament through the skin of a patient.

SUMMARY OF THE INVENTION

A multi-site injection system in accordance with the present invention generally includes a plurality of medicament delivering needles/microprotrusions along with a support therefore. A supply of medicament is provided and a means provided for supplying the medicament to the plurality of needles/microprotrusions in order to effect delivery into a stratum corneum of a user.

One embodiment of the present invention generally includes a rotatable drum having an outer surface with the microprotrusions thereon.

The microprotrusions may include passages, or lumens, therethrough for enabling transport of the medicament therethrough from an inner surface of the rotatable drum and into the stratum corneum of a user. Alternatively the microprotrusions may be solid and coated with the medicament.

A fixed inner drum may be provided for supporting the rotatable drum and includes at least one radial opening therein for providing the medicament to the microprotrusions.

The supply of medicament is disposed within the inner drum and a housing is provided for supporting the rotatable drum and the inner drum. The housing includes an opening for exposing an arcuate portion of the rotatable drum in order to enable rotation of the rotatable drum by rolling the rotatable drum against a users skin.

While not shown, a blatter may be provided for containing the medicament with the blatter being in fluid communication with the radial opening in a fixed inner drum for providing the medicament to the microprotrusion passages.

An alternative embodiment of a multi-site injection system in accordance with the present invention generally includes a guide plate having a plurality of openings therethrough and needle plate having a plurality of needles projecting therethrough with each needle being aligned with a corresponding opening and a guide plate.

The needle plate is movable from a first position with the needles position behind a top surface of the guide plate to a second position with the needles projecting from the top plate through the openings. A plunger base is provided for moving the needle plate from the first to the second position.

The needles may be coated with a medicament or the needles may include lumens in communication with a medicament reservoir, or supply, disposed in the plunger base for delivery of the medicament into a stratum corneum of a users skin.

The needles and openings may be arranged in order to applicate the medicament to a users skin in a definite pattern which, may be a symmetrical radial pattern, an asymmetrical radial pattern or a concentric pattern which may or may not be circular. A rectilinear pattern of needles may be utilized in accordance with the present invention and the medicament preferably comprises botulinum toxin.

A further embodiment of a multi-site injection system in accordance with the present invention generally includes a needle plate and a plurality of hollow needles fixed to an outside of the needle plate, for transport of a medicament from an inside of the needle plate and into a stratum corneum of a user.

A pressurizer is provided and disposed over an inside of the needle plate to form a cavity therebetween in communication with the hollow needles.

In addition, an injection port is disposed in the pressurizer for introducing the medicament into the cavity.

More particularly, in accordance with the present invention, the pressurizer is flexible for causing uniform transport of the medicament through the needles.

Accordingly, the pressurizer provides a means for forcing the medicament from the cavity through needle lumens.

A still further embodiment of a multi-site manifold injection system in accordance with the present invention generally includes a handle along with a syringe supported by the handle and including a plunger for dispensing a fluid medicament from the syringe.

A manifold is attached to one end of the handle and in fluid communication with a syringe and a plurality of needles, protruding from the manifold, are provided for delivery of the fluid medicament from the manifold and into the stratum corneum of a user.

In accordance with one embodiment of the present invention, the manifold may be disposed perpendicular to the handle and further comprise a plurality of concentric conduits interconnected with radial conduits.

The concentric conduits may be circular and radially spaced apart from one another.

In addition, a transparent sheet may be provided and interconnecting a concentric and radial conduits for enabling visual orientation of the manifold onto a patients' skin by manipulation of a handle.

Alternatively, the manifold may comprise a plurality of concentric conduits and a plurality of radial ribs supporting the plurality of concentric conduits. Preferably, the medicament utilized in combination with the syringe manifold and needle is botulinum toxin.

Yet another embodiment of the present invention includes a multi-site blister injection system having a carrier sheet including a plurality of medicament filled rupturable blister disposed on an inside surface thereof.

A plurality of needles extending from the outside of the carrier stream may be provided with each needle being aligned with a corresponding blister and having a lumen for transport of the medicament into the stratum corneum of the user.

Each of the needles is positioned for traversing the carrier sheet and rupturing the corresponding blister.

A pressure plate is disposed on the carrier sheet inside surface for forcing a blister against the needles for causing rupture thereof and forcing a medicament through the needle lumens.

The pressure plate may be fixed to the carrier sheet and a foam pad may be disposed on the carrier sheet outside. Preferably, the foam pad covers the needles extending the carrier sheet outside and is penetrable by the needles.

The foam pad may be adhered to the pressure plate along a perimeter thereof for securing the carrier sheet between the foam pad and the pressure plate. Preferably, the medicament in accordance with the present invention comprises botulinum toxin.

Still another embodiment of a multi-site injection system in accordance with the present invention generally includes a shell including a top and a bottom and a plurality of needles protruding from the shell bottom. Each of the needles include a lumen extending through the shell bottom.

A membrane is provided and disposed between the shell top and the shell bottom and an inlet is provided for introducing a fluid between the shell top and the shell bottom.

A diverter is also provided for selectively directing fluid between the membrane and the shell bottom and between the membrane and the shell top.

The diverter may include a manually operated valve and the system may further include the supply of medicament, preferably botulinum toxin, for introduction between the membrane and the shell bottom.

An inert fluid supply may also be provided for introduction between the membrane and the shell top.

Also in accordance with the present invention, a method of multi-site injection comprises providing a shell between the top and a bottom with bottom having a plurality of needles protruding therefrom with each needle including a lumen therethrough and extending through the shell bottom.

The method also includes providing a membrane between the shell top and the shell bottom.

More particularly, in accordance with the present invention, the method includes introducing a medicament between the membrane and the shell bottom and introducing a pressurized fluid between the membrane and the shell top for forcing the medicament through the needle lumens.

The medicament in accordance with the present invention preferably comprises botulinum toxin.

BRIEF DESCRIPTION OF THE DRAWINGS

The advantages and features of the present invention will be better understood by the following description when considered in conjunction with the accompanying drawings in which:

FIG. 10 is a perspective view of a multi-site injection system in accordance with the present invention generally showing a needle plate with a plurality of needles projecting therefrom and fixed to an outside surface of the needle plate;

FIG. 11 is a perspective view of the multi-site injection system shown in FIG. 1 showing a reverse side with a pressurizer disposed over an inside of the needle plate along with an injection port and a pressurized reservoir of medicament interconnected to the port via a tube;

FIG. 12 is a partial cross section of the injection system shown in FIGS. 10 and 11 illustrating a cavity for and between the pressure plate and an inside surface of the needle plate illustrating medicament flow from the pressure reservoir through the tube into the cavity and through hollow needles for transport of the medicament into a stratum corneum of a user;

DETAILED DESCRIPTION

Figure 1:
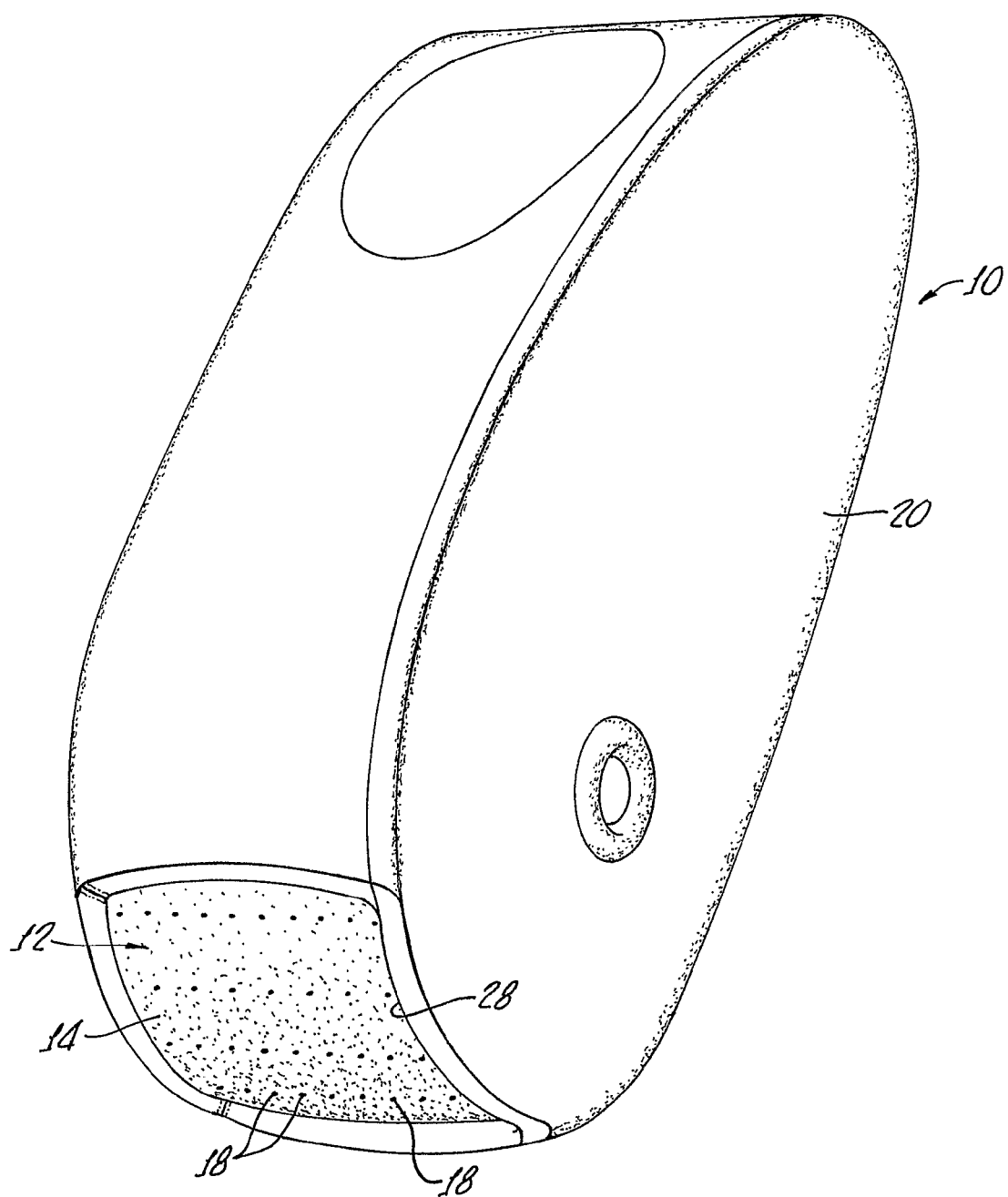
FIG. 1 is a perspective view of a multi-site injection system in accordance with the present invention generally showing a housing, or shell, for supporting a rotatable drum along with a rotatable drum having an outer surface with microprotrusions therein, a port is also shown which provides an access for charging the system with a medicament to be injected, such as, for example botulinum toxin.

With reference to FIG. 1, there is shown a multi-site injection system 10 which includes a rotatable drum 12 including an outer surface having a plurality of microprotrusions, or needles, affixed thereto. The microprotrusions may have lumens, or passages, therethrough.

Figure 2:
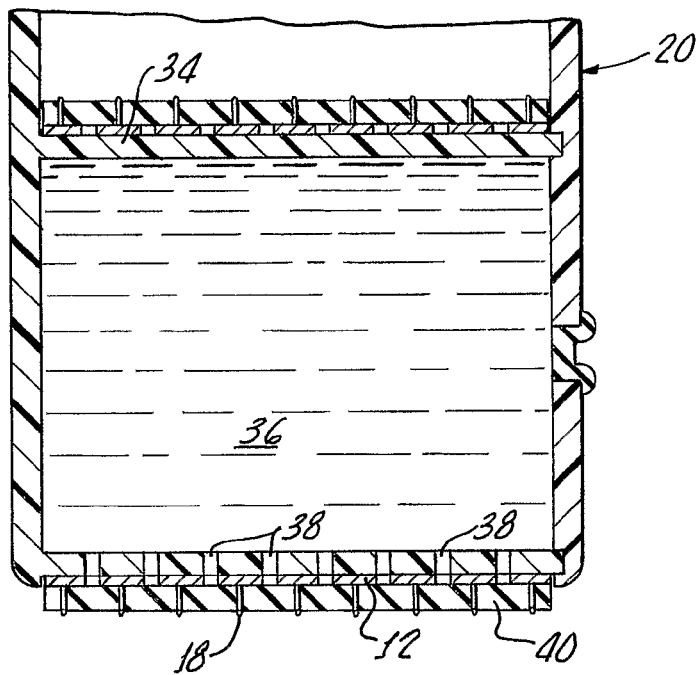
FIG. 2 is a partial cross section of the system shown in FIG. 1 more clearly illustrating a fixed inner drum for containing a medicament and at least one radial opening therein for providing medicament to a plurality of microprotrusions affixed to and rotatable with the rotatable drum, the rotatable drum is rotated by rolling the drum against a users skin, not shown, and the housing supporting the rotatable drum and the inner drum includes an opening for exposing an arcuate portion of the rotatable drum for enabling rotation thereof.
Figure 3:
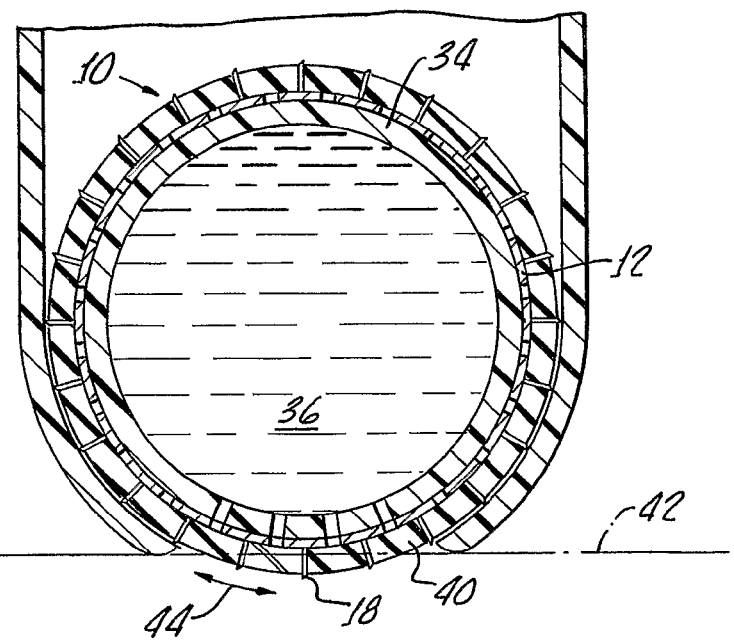
FIG. 3 is a cross sectional view taken along line 3-3 of FIG. 2 more clearly showing operation of the system.

A housing 20 is provided for supporting the rotatable drum along with a fixed inner drum 34, see FIGS. 2 and 3. An arcuate opening 28 in the housing 20 is provided for exposing the drum surface 14 which enables rotation of the drum 12 by rolling the drum 12 against a users skin 42.

Also provided is an access port for introducing a medicament, such as botulinum toxin into the system via a syringe, not shown, or other suitable conveyance.

As more clearly shown in FIGS. 2 and 3, an inner drum, fixed to the housing, or shell, 20, is provided for containing a supply of medicament instilled through the access port as hereinabove noted.

This nonrotating inner drum, or reservoir, 36 includes a plurality of radial passages, or openings, 38 for providing the medicament 36 to the needles 18.

Preferably, a sponge-like material 40 is disposed on the rotatable drum 12 for both distributing medicament provided through radial openings 38 and enabling application of the medicament via the needles 18 without excess medicament being deposited on the user's skin 42.

In operation, rotation of the drum 12 on the users skin 42 causes rotation of the drum as indicated by the arrow 44 and medicament flows into the sponge and is applied to the users skin 42. The needles penetrate the stratum corneum, or skin, 42 of the user, thus introducing the medicament thereinto.

Alternatively, the protrusions, or needles, may include lumens therethrough for direct transport of medicament 36 from the inner drum 34 upon rotation of the drum 12 against the users skin 42.

Figure 4:
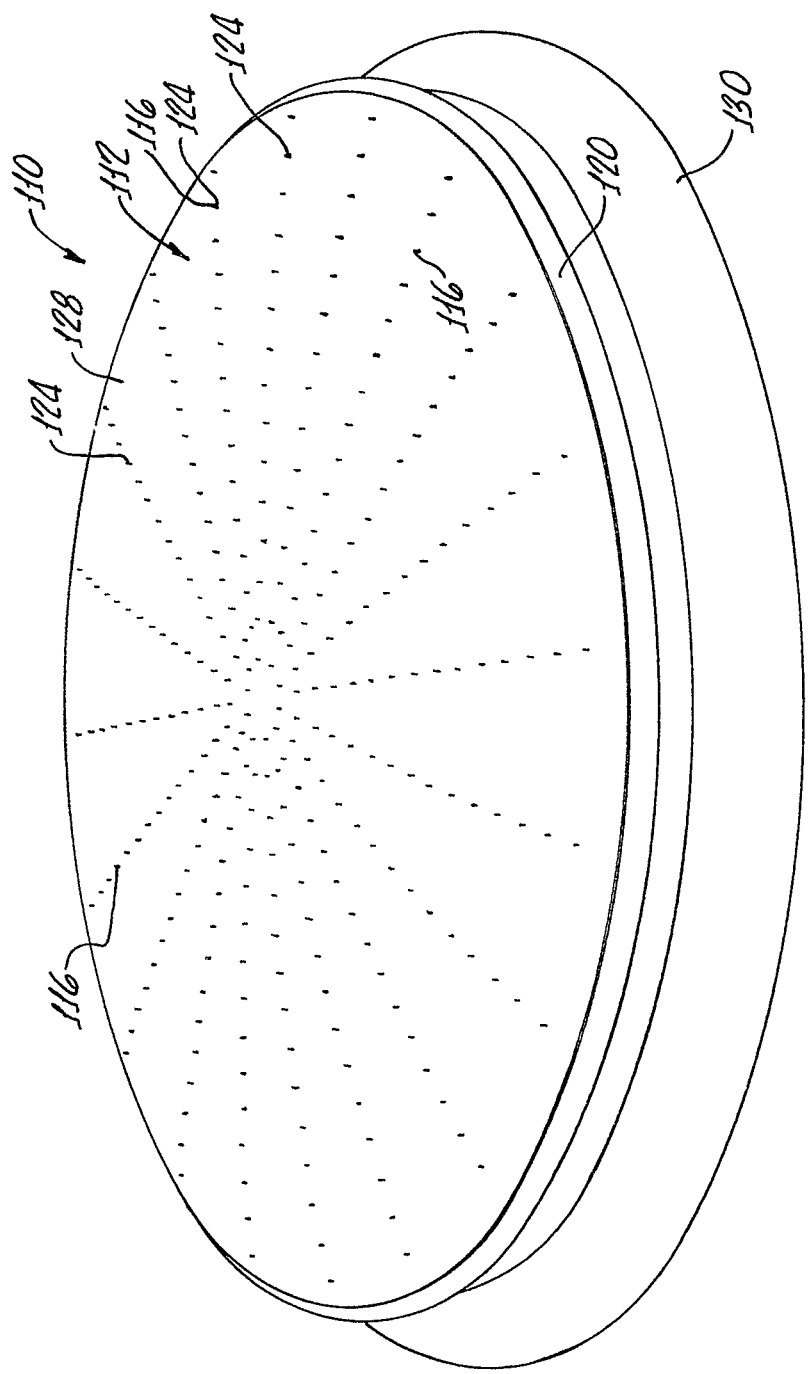
FIG. 4 is a perspective view of a multi-site injection system in accordance with the present invention generally showing a guide plate having a plurality of openings therethrough, a plunger base and a plurality of needles projecting from the guide plate.

With reference to FIG. 4, there is shown an injection system 110 generally including a guide plate 112 having a plurality of openings therethrough along with a needle plate 120 including a plurality of needles 124 shown extending through the openings 116 and projecting from a top surface 128 of the guide plate 112. Also shown is a plunger base 130 for moving the needle plate from a first position with the needles 124 positioned generally behind the top surface 128, see FIG. 5 to a second position with the needles 124 projecting from the top surface 128 as shown in FIGS. 4, 5, and 6.

The needles 124 may be coated with a medicament, such as, for example, botulinum toxin.

The guide plate 112, needle plate 120, needles 124, and base 130 may be made form any suitable material and the needles preferably are about 128 gauge and 1 mm in length. Use of the multi-site injection system 110 for delivery of a medicament into the stratum corneum of a users skin is illustrated in FIGS. 5-7.

Figure 5:
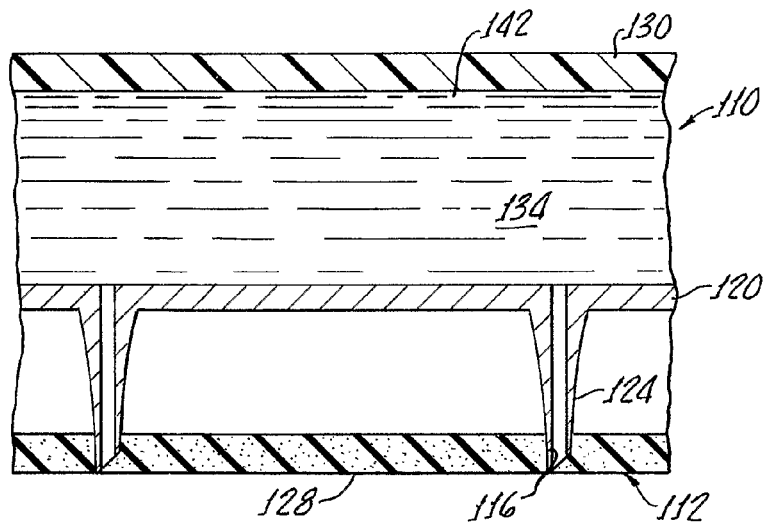
FIG. 5 is a partial cross section of one embodiment of the present invention showing a reservoir of medicament disposed in the plunger base with needle lumens in fluid communication therewith and disposed with needle points generally flush with a top surface of the guide plate.
Figure 6:
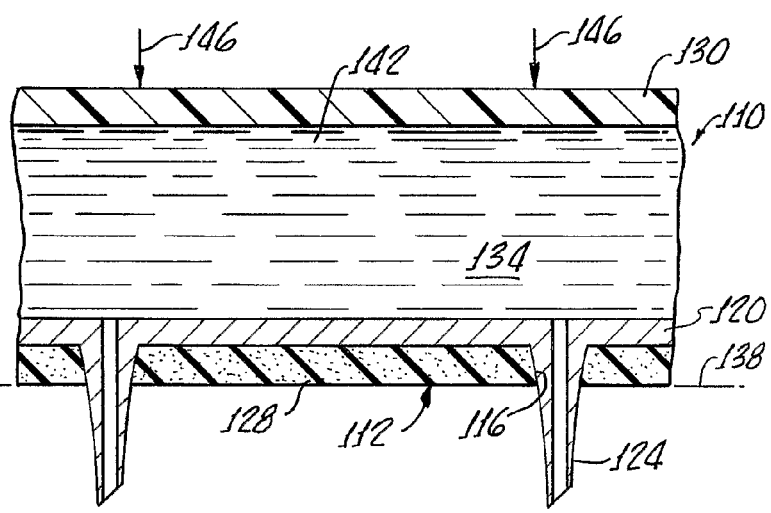
FIG. 6 is a cross sectional view similar to that shown in FIG. 5 illustrating movement of the plunger base for protruding the needles from the top surface of the guide plate and into a stratum corneum of a users skin.
Figure 7:
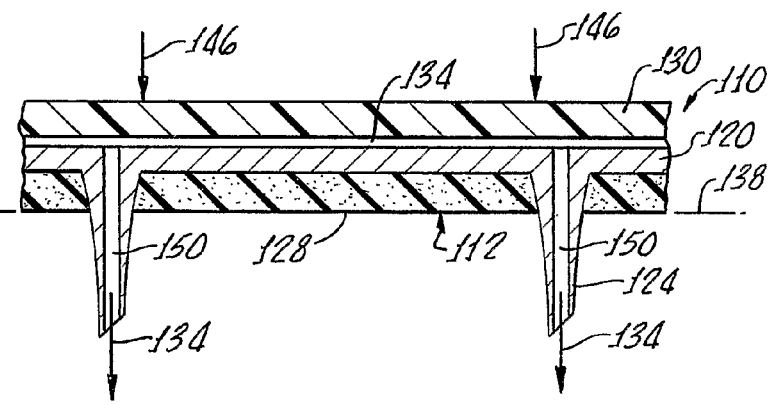
FIG. 7 illustrates continued pressure on the plunger base for forcing medicament through the needle lumens and into the stratum corneum of the users skin.

As shown, the needle plate is configured in any suitable manner for being moveable from a first position shown in FIG. 5 with the needles positioned behind, or flush with the top surface 128 of the needle plate 120 to a second position shown in FIGS. 6 and 7 with the needles 124 projecting from the top surface 128 through the openings 116.

The plunger base 130 preferably includes and defines a reservoir 142 between the needle plate 120 and the base 130 for containing the medicament 134.

Incompressibility of the medicament 134 enables movement of the plunger base 130 to move the needle plate 120 from the first to the second position as indicated by the arrows 146.

Continued movement of the plunger base 130 forces medicament 134 through needle lumens 150 and collapse of the reservoir 142. The guide plate 112, needle plate 120, and plunger based 130 may be integrally formed with a diaphragm arrangement, not shown, for enabling the relative motion hereinabove described. Other suitable configurations should be considered to be within the scope of the present invention.

Figure 8:
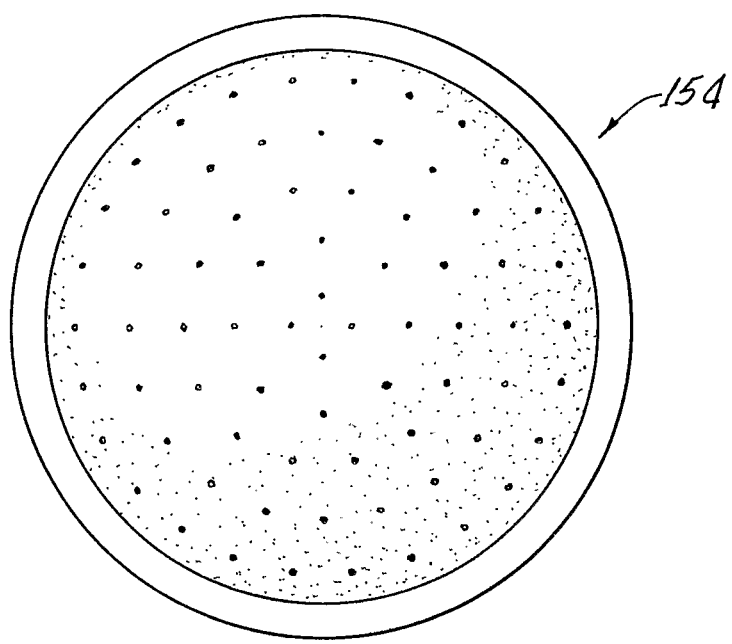
FIGS. 8 and 9 illustrate various needle patterns which may be suitable for various applications and areas of treatment on a users skin.
Figure 9:
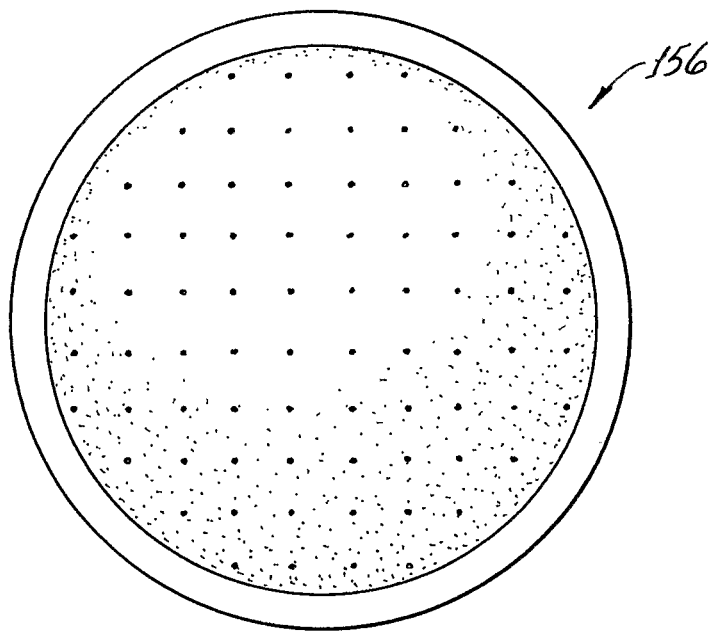

It should be appreciated that while the system 110 shown in FIG. 4 illustrates, holds, or openings 116 and needles arranged in a generally symmetrical radial pattern, other patterns may be utilized for delivery of a medicament to body areas requiring different patterns of application. FIGS. 8 and 9 illustrate systems 154, 156 showing an asymmetrical radial pattern and a rectilinear pattern respectively.

With reference now to FIGS. 10 and 11, there is shown a multi-site injection system 208 in accordance with the present invention generally including a flexible needle plate 210 having a plurality of hollow needles 212 fixed to an outside surface 216 of the needle plate 210. The needle plate 210 may be formed from any suitable material and the needles may be formed thereinto or affixed thereto in any conventional manner.

As more clearly shown in FIG. 11, the system 208 may include a pressurizer 220, which may be in the form of a flexible blatter or the like, for causing uniform pressure across an inside surface 224 of the needle plate 210.

As shown in FIG. 12, the pressurizer 220 establishes a cavity 226 between the pressurizer 220 and the inside surface 224 of the needle plate 210.

The pressurizer 220 provides a means for forcing medicament, which is preferably botulinum toxin from the cavity 226 through needle lumens 232. Spacing an orientation of the needles on the needle plate 210 is determined by the intended use of the needle plate 210 on specific user body parts, not shown.

An injection port 234 is preferably interconnected to a pressure reservoir 236 through a tube 240. Control of medicament flow from the pressure reservoir 236 through the tube and into the cavity 226 may be controlled in any conventional manner.

Pressure medicament in the cavity 226 thus forces the medicament into a stratum corneum 242 of a user, not shown.

Pressure provided by the flexible pressurizer as indicated by the arrows 244, 246 enable uniform flow of medicament as indicated by arrows 248, 250 through the needle lumens 232 as indicated by arrows 252, 254.

Figure 13:
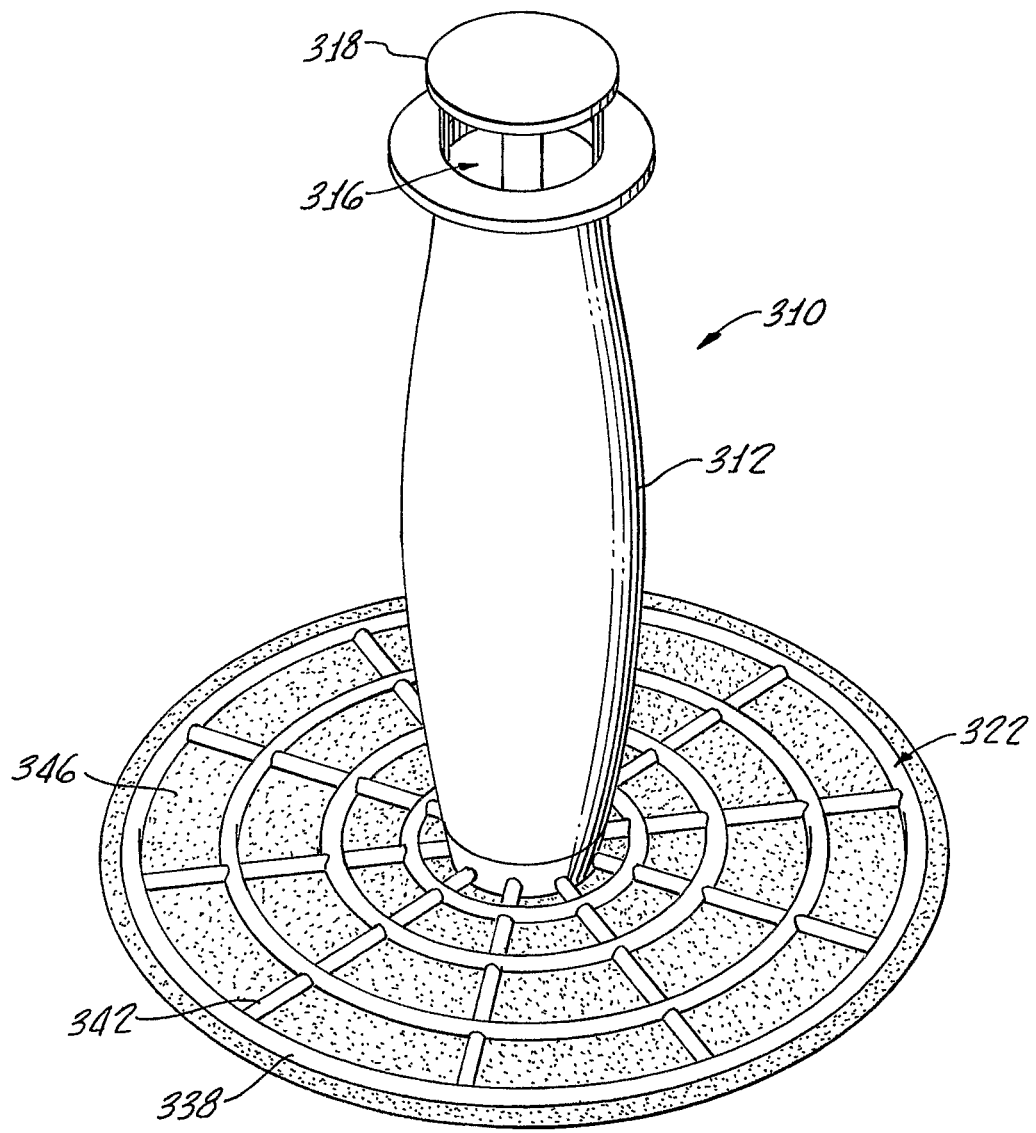
FIG. 13 is a perspective view of the multi-site manifold injection system in accordance with the present invention generally showing a handle, a manifold attached to one end of the handle and a plurality of needles protruding from the manifold for delivery of fluid medicament from the manifold into a stratum corneum of a user, not shown.
Figure 14:
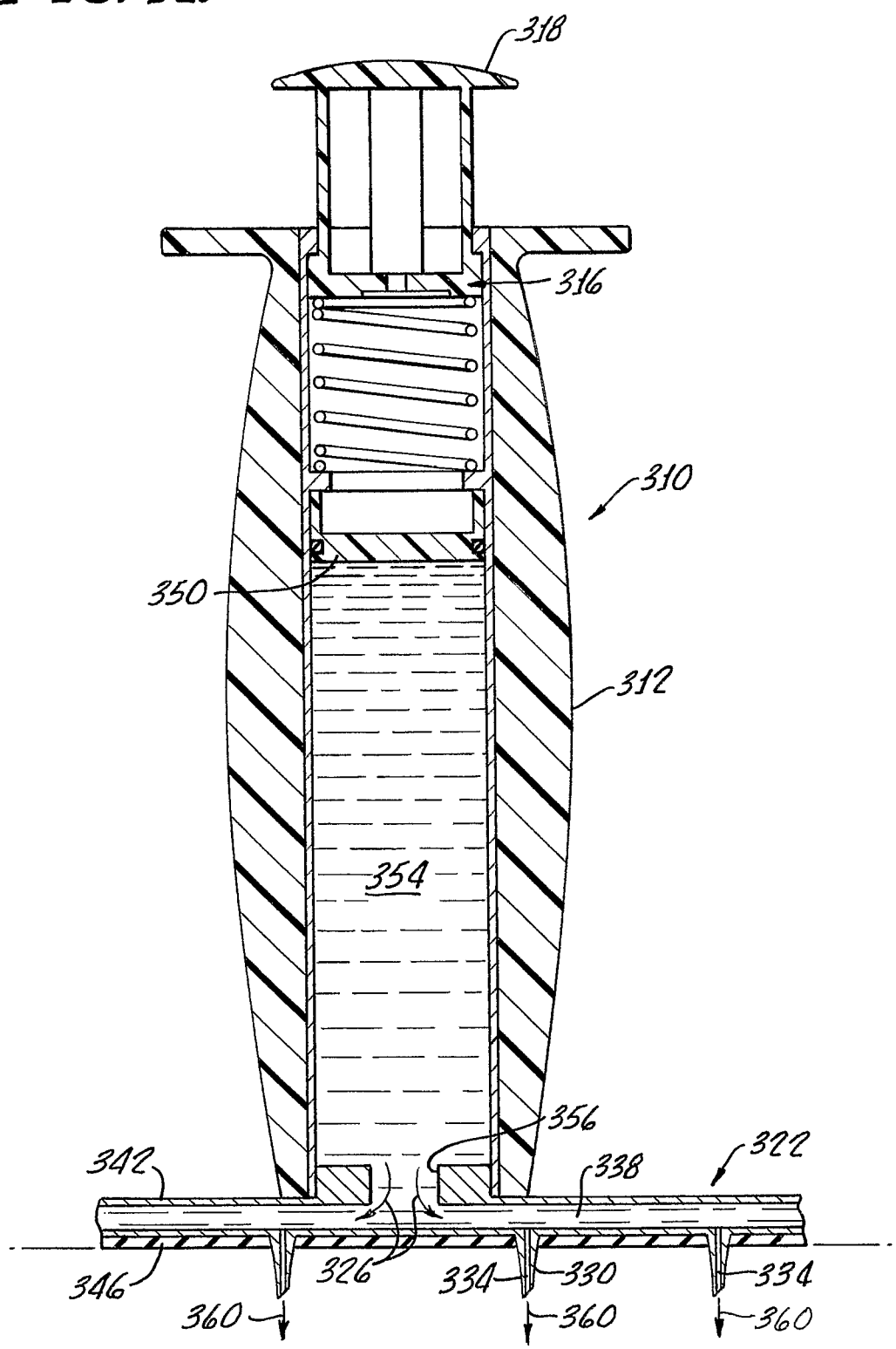
FIG. 14 is a cross sectional view of the system shown in FIG. 13 more clearly shown a syringe supported by the handle and including a plunger for dispensing the fluid medicament from the syringe.

With reference to FIGS. 13 and 14, there is shown a multi-site injection system 310 including a handle 312, a syringe 316, which includes a plunger 318 for dispensing a fluid medicament from the syringe and into a manifold 322, as illustrated by arrows 326 in FIG. 14.

The handle 312, syringe 316, plunger 318, and manifold 322 may be formed by any suitable materials. As shown in FIGS. 13 and 14, the manifold 322 may be disposed in a generally perpendicular relationship with the handle 312 and plunger 318 and a plurality of needles 330 protruding from the manifold 322 for delivery of fluid medicament from the manifold 322 into a stratum corneum of a user (not shown).

The needles may be affixed to the manifold 322 in any conventional manner may be approximately 328 gauge with a length of approximately 1 mm and include needle lumens 334 in fluid communication with conduits 338 of the manifold 322. The conduits may be concentric and in fluid communication with radial members 342.

In one embodiment of the present invention, the radial members may be hollow for providing fluid communication of medicament or alternatively in another embodiment of the present invention may be solid ribs for supporting the conduits 338.

A transparent sheet 346 may interconnect the conduits 338, 342 for enabling a constant pressure to be exerted over the entire area presented by the manifold 322 while enabling visual orientation of the manifold 322 onto a patients' skin (not shown) by manipulation of the handle 312.

In operation, finger pressure on the plunger 318 drives, or otherwise ratchets, a piston 350 disposed within the syringe for forcing medicament 354 downwardly through an exit port 356 and into the manifold conduits 338, as hereinabove noted, forcing medicament through the needle lumens 334 as indicated by the arrows 360. It should be appreciated that any suitable plunger, syringe, which may be fitted into the handle of the present invention is to be considered within the scope of the present invention.

Figure 15:
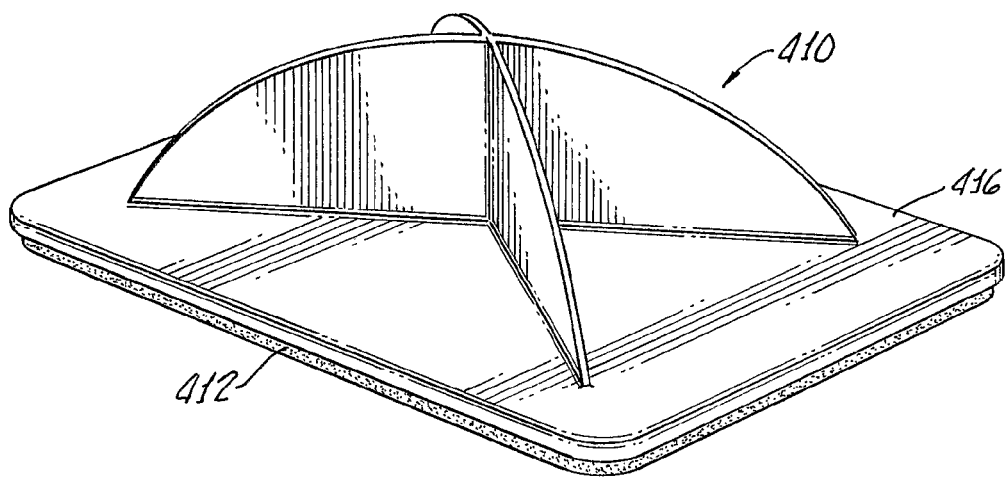
FIG. 15 is a perspective view of a multi-site blister injection system in accordance with the present invention generally showing a carrier sheet and a pressure plate disposed on an inside surface of the carrier sheet.
Figure 16:
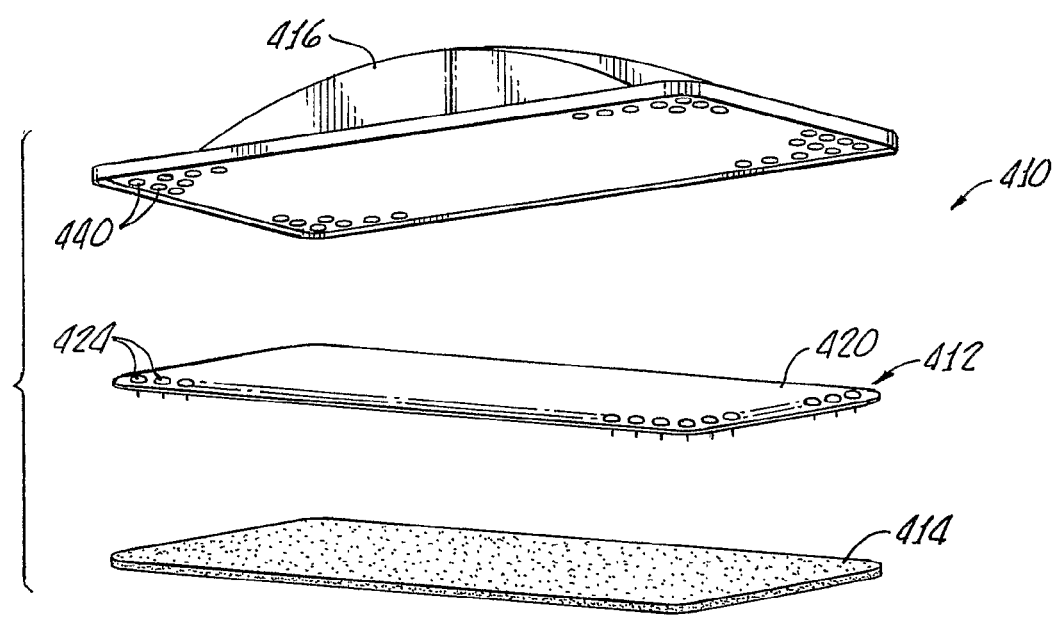
FIG. 16 is an exploded perspective view of the system more clearly illustrating a carrier sheet with medicament filled blisters and a foam pad.

With reference to FIGS. 15 and 16, there is shown a multi-site injection system 410 in accordance with the present invention showing a carrier sheet 412 along with a foam pad 414, see FIG. 16. A pressure plate 416 is disposed on a carrier sheet inside surface 420 and the foam pad 414 may include an adhesive for holding the carrier sheet 412 against the pressure plate 416.

Figure 17:
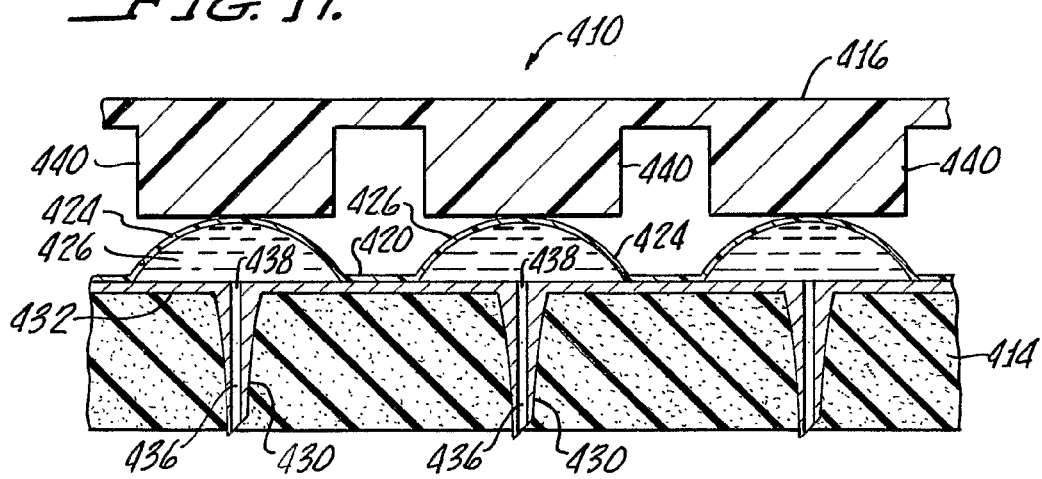
FIG. 17 is a cross sectional view of the embodiments shown in FIGS. 15 and 16 more clearly illustrating a plurality of needles extending from the carrier sheet, a plurality of rupturable blisters filled with a medicament, such as botulinum toxin, along with the pressure plate positioned for forcing the blisters against corresponding needles for causing rupture thereof and forcing medicament through needle lumens.
Figure 18:
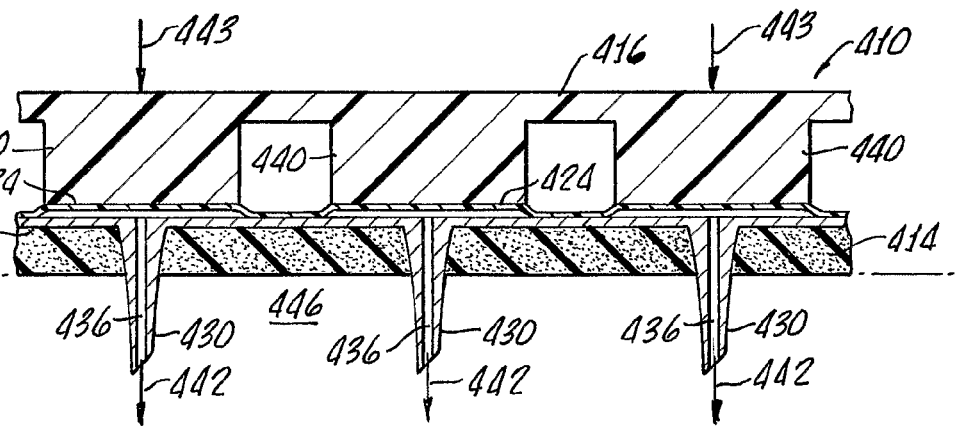
FIG. 18 is a cross sectional view similar to that shown in FIG. 17 in which the pressure plate has been forced against the blisters and medicament is forced into the stratum corneum of a users skin.
Figure 19:
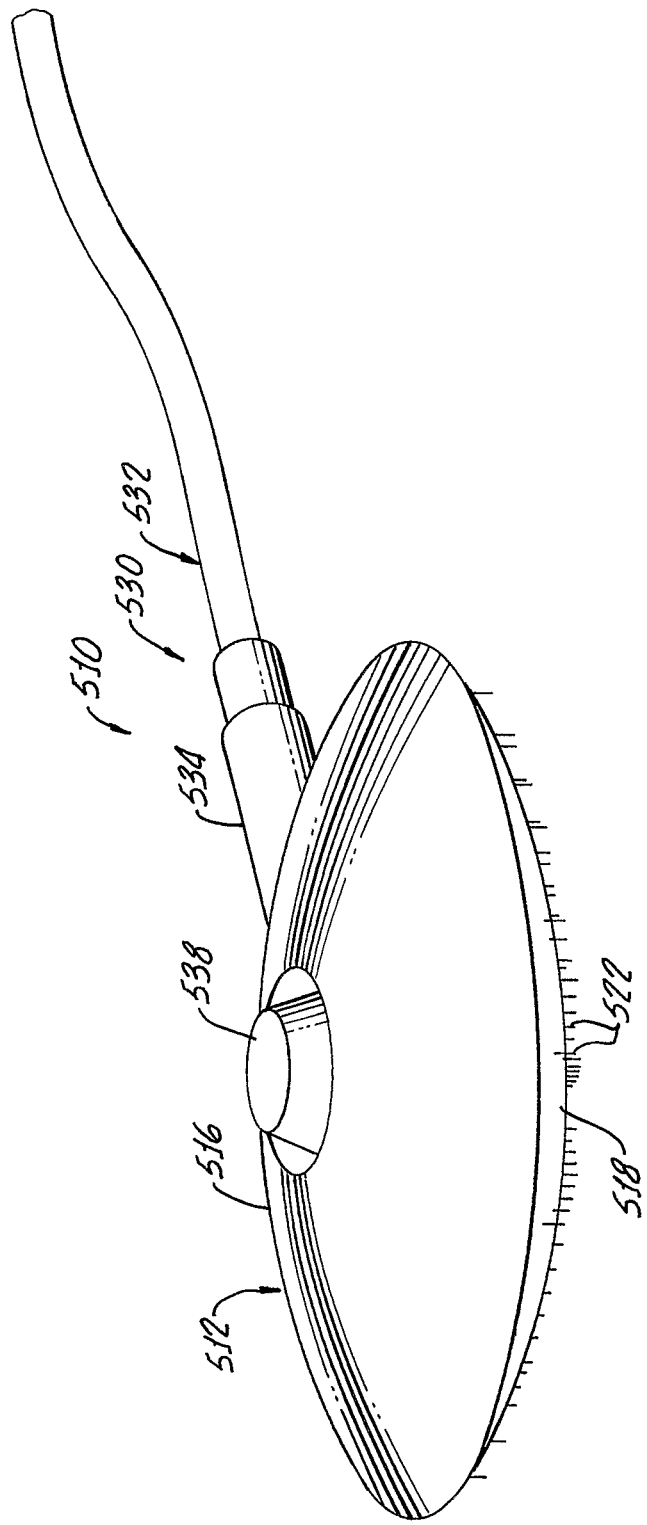
FIG. 19 is a perspective view of a multi-site injection system in accordance with the present invention generally illustrating a shell having a top and a bottom with a plurality of needles protruding from the shell bottom. An inlet for introducing fluid between the shell top and bottom is shown along with a diverter.
Figure 20:
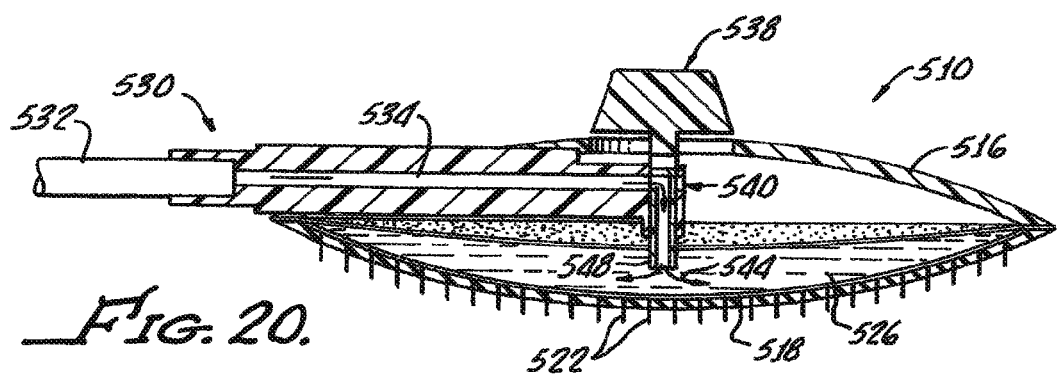
FIG. 20 is a cross sectional view of the system shown in FIG. 19 more clearly illustrating the shell top, bottom and a membrane disposed between the shell top and the shell bottom along with a diverter valve for selectively directing fluid between the membrane and the shell bottom and between the membrane and the shell top, FIG. 20 showing a filling cycle with medication being injected into a reservoir.
Figure 21:
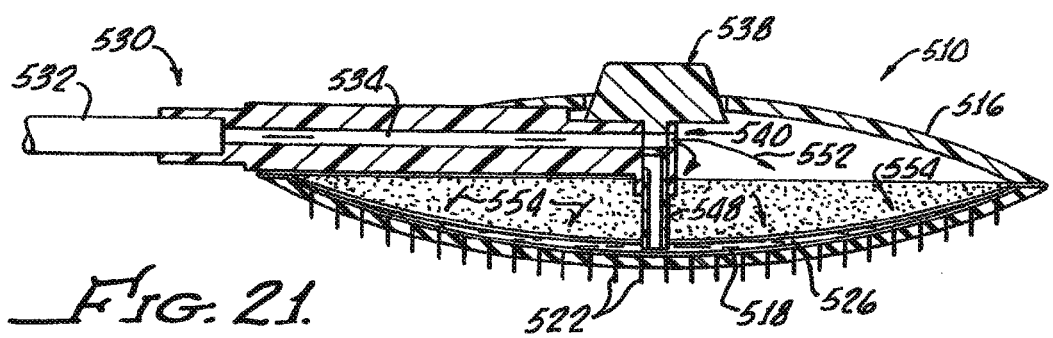
FIG. 21 is a cross sectional view similar to FIG. 20 showing the diverter selectively directing fluid between the membrane and top shell during an injection cycle in order to pressurize the reservoir of medicament thereby forcing the medicament through needle lumens.
Figure 22:
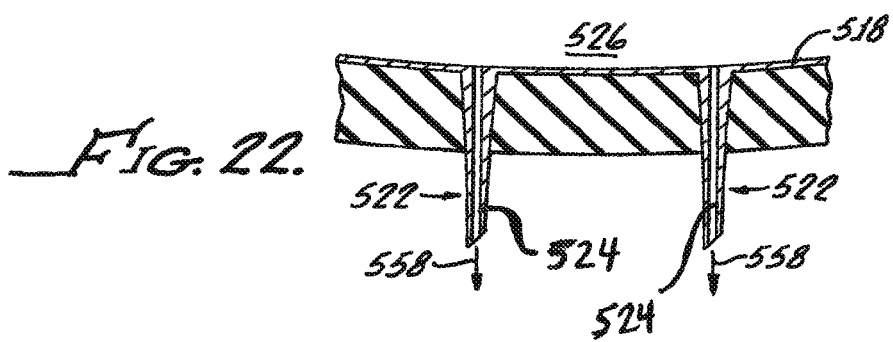
FIG. 22 is an enlarged view of the needles illustrating a lumen therethrough for injection of the medicament into the stratum corneum of a users skin (not shown).

With reference to FIGS. 17 and 18, the carrier sheet 412 may be of conventional design and include blisters 424 filled with a medicament 426 as well as a plurality of protruding needles 430 extending from an outside surface 432 of the carrier sheet 412. Each of the needles which may be, for example, 428 gauge and having 2 mm length and include lumens 436 for transport of medicament therethrough.

Each of the needles 430 is aligned with a corresponding blister 424 and each needle including a point 438 for rupturing of corresponding blisters 424.

As shown, the pressure plate preferably includes a plurality of berms 440 for providing enhanced pressure against blisters as the pressure plate 416 is forced against the blisters 424.

The foam pad 414 preferably has a depth equal to or slightly greater than the length of the needles 430 in order to prevent inadvertent contact with the needles before use.

In operation, as shown in FIG. 18, when the pressure plate 416 is forced downwardly a indicated by the arrows 443, the needle points 438 are rupture the blusters 424 and continued pressure by the pressure plate 416 collapses the cavity 226 through needle lumens 232. Spacing and orientation of the needles on the needle plate 210 is determined by the intended use of the needle plate 210 on specific user body parts, not shown.

This pressure also compresses the foam pad 414 as shown against a users skin 444 and into the stratum corneum 446. It should be appreciated that the drawings are not to scale but rather enlarged to illustrate the operation of the multi-site injection system 410.

With reference to FIGS. 19-22, there is shown a multi-site injection system 510 in accordance with the present invention generally including a shell 512 having a top 516 and a bottom 518. A plurality of needles 522 protrude from the shell bottom 518 with each needle 522 including a lumen 524 (see FIG. 22) communicating with a reservoir 526 established by a membrane 528 disposed between the shell top 516 and the shell bottom 518.

It should be appreciated that the shell, membrane and needles may be made from any suitable material. Preferably, the needles have a gauge of about 528 and a length in the order of 2 mm. An inlet 530 including a tube 532 and passageway 534 provide a means for introducing a fluid between the shell top 516 and shell bottom 518.

A diverter 538 includes a manually operated valve 540 for selectively directing fluid between the membrane 528 and shell bottom 518 into the reservoir 526.

As shown by the arrow 544 during a filling cycle the inlet, or supply line, introduces a medicament, preferably botulinum toxin, into the reservoir by alignment with a dip tube 548 with the passageway 534 for filling of the reservoir 526.

Thereafter, the diverter 538 by way of the valve 540 aligns the passageway 534 for introducing a fluid, such as saline solution, between the membrane 528 and the top shell as illustrated by the arrows 552, 554. This provides a pressure above the membrane 528 which forces the medicament from the reservoir 526 through the needle lumens 524 as illustrated by the arrows 558.

Although there has been hereinabove described various multi-site remotely pressurized injection systems in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A multi-site injection system comprising:
    a rotatable drum having an outer surface with microprotrusions thereon, for penetrating a stratum corneum of a user, said rotatable drum including a sponge-like material;
        a fixed inner drum containing a supply of medicament, the fixed inner drum having at least one radial opening therein for providing said medicament to the sponge-like material; and
        a housing for supporting the rotatable drum and the inner drum, said housing having an opening for exposing an arcuate portion of said rotatable drum in order to enable rotation of said rotatable drum by rolling said rotatable drum against a user's skin, the opening being configured such that a majority of the rotatable drum surface remains covered by the housing during the rotation of said rotatable drum;
    wherein each of said microprotrusions of the rotatable drum protrude beyond an outermost surface of the sponge-like material when the sponge-like material is in an uncompressed state.

2. The multi-site injection system of claim 1 wherein the microprotrusions include lumen therethrough for direct transport of medicament from the inner drum upon rotation of the drum against a user's skin.

3. The multi-site injection system of claim 1 wherein the exposed arcuate portion of the rotatable drum is defined by an arc of the rotatable drum, the arc being not greater than about 90 degrees.

4. The multi-site injection system of claim 1 wherein the medicament is botulinum toxin.

* * * * *